(12) United States Patent

Shirai et al.

(10) Patent No.: US 7,553,865 B2
(45) Date of Patent: Jun. 30, 2009

(54) INDOMETHACIN EXTERNAL PREPARATION

(75) Inventors: Hiroyuki Shirai, Tokyo (JP); Tatsuya Nakai, Fuji (JP); Masami Serizawa, Numazu (JP); Yasuo Shinoda, Shizuoka (JP); Toshio Inagi, Mishima (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 509 days.

(21) Appl. No.: 10/521,958

(22) PCT Filed: Jul. 22, 2003

(86) PCT No.: PCT/JP03/09273

§ 371 (c)(1),
(2), (4) Date: Jan. 21, 2005

(87) PCT Pub. No.: WO2004/010994

PCT Pub. Date: Feb. 5, 2004

(65) Prior Publication Data

US 2005/0239868 A1 Oct. 27, 2005

(30) Foreign Application Priority Data

Jul. 29, 2002 (JP) .............................. 2002-219315

(51) Int. Cl.
 A61K 31/40 (2006.01)
 A01N 43/38 (2006.01)
 C07D 209/26 (2006.01)
(52) U.S. Cl. ...................................... 514/420; 548/500
(58) Field of Classification Search ........................ None
 See application file for complete search history.

(56) References Cited

U.S. PATENT DOCUMENTS 4,309,414 A * 1/1982 Inagi et al. .................. 514/420
4,474,798 A 10/1984 Inagi et al.
4,545,992 A 10/1985 Kamishita

FOREIGN PATENT DOCUMENTS

| EP | 0 055 029 | 6/1982 |
|---|---|---|
| JP | 57-126414 | 8/1982 |
| JP | 58-185514 | 10/1983 |
| JP | 59-227818 | 12/1984 |
| JP | 61-200907 | 9/1986 |
| JP | 62-061918 | 3/1987 |
| JP | 01-279831 | 11/1989 |
| JP | 05-271075 | 10/1993 |
| JP | 10-182458 | 7/1998 |
| JP | 2001-354548 | 12/2001 |
| JP | 2003-095985 | 4/2003 |

OTHER PUBLICATIONS

Sigma Aldrich Catalogue. Poly(ethylene glycol) 6000. catalogue # 81260. Properties Information.*
Sigma Aldrich Catalogue. 2007. Poly(ethylene glycol) 6000. catalogue # 81260. Properties Information, p. 1.*

* cited by examiner

Primary Examiner—Sreeni Padmanabhan
Assistant Examiner—Samira Jean-Louis
(74) Attorney, Agent, or Firm—Knobbe, Martens, Olson & Bear, LLP

(57) ABSTRACT

An object of the present invention is to provide an indomethacin external preparation that has an excellent use feeling and excellent absorbability and causes no phase separation into an oil layer and an aqueous layer, thus exhibiting satisfactory stability of preparation with time. Provided is an indomethacin external preparation containing: 0.1 to 3 wt % of indomethacin; 25 to 50 wt % of alcohol; 0.01 to 5 wt % of gelling agent; 5 to 30 wt % of oil component; 20 to 50 wt % of water; and 0.01 to 10 wt % of one or more components selected from the group consisting of glyceryl monostearate, sorbitan monostearate, stearyl alcohol, and polyethylene glycol monostearate.

2 Claims, No Drawings

INDOMETHACIN EXTERNAL PREPARATION

RELATED APPLICATIONS

This application is the U.S. National Phase under 35 U.S.C. § 371 of International Application PCT/JP2003/009273, filed Jul. 22, 2003, which was published in a language other than English, which claims priority of Japanese Patent Application No. 2002-219315, filed Jul. 29, 2002.

TECHNICAL FIELD

The present invention relates to an indomethacin external preparation that has an excellent use feeling and excellent absorbability of indomethacin and undergoes no phase separation with time so that it can well retain a stable state.

BACKGROUND ART

As external preparations containing indomethacin, those of various preparation forms such as a gel formulation, a cream formulation, a liquid formulation, and a poultice formulation are commercially available and those preparations have respective characteristics inherent to the preparation forms.

For example, gel formulations contain a large amount of alcohol so that they dissolve indomethacin well therein and exhibit excellent absorbability through a skin. However, when in use, they cause irregularities (a phenomenon in which a polymer collects like grime when the polymer is coated by rubbing) so that the formulations provide a poor use feeling. On the other hand, cream formulations are blended with a sufficient amount of oil so that after they are used, they do not stick, giving an excellent use feeling. However, because of insufficient solubility of indomethacin therein, the cream formulations exhibit poor absorbability of indomethacin through a skin as compared with that of the gel formulations.

Accordingly, it has been desired to develop a so-called gel-cream formulation that has advantages of both a gel formulation and of a cream formulation, i.e., a satisfactory use feeling and satisfactory absorbability of indomethacin through a skin and for this purpose many studies have been made.

Usually, a surfactant is compounded in a cream formulation in order to prevent phase separation, i.e., separation into an oil layer and an aqueous layer. However, compounding a large amount of alcohol to a cream formulation results in the phase separation of the preparation into an oil layer and an aqueous layer with time since the alcohol inhibits the emulsifying action of the surfactant. In addition, compounding a gelling agent to a cream formulation in such an amount that irregularities will not occur can hardly prevent such phase separation of the preparation with time.

There have been known some prior art documents that report gel-cream formulations containing indomethacin, for example, JP 58-185514 A, JP 59-227818 A, JP 57-126414 A, and JP 1-279831 A. However, the preparation disclosed in JP 58-185514 A has an alcohol content of 10 wt % or less, so that the solubility and percutaneous absorbability of indomethacin are poor. The preparations disclosed in the other prior art documents are unsatisfactory since they cause irregularities specific to gel formulations or phase separation of the preparations.

In view of those drawbacks, it has been demanded to provide an indomethacin external preparation that has an excellent use feeling and excellent absorbability of indomethacin and that undergoes no phase separation of the preparation with time so that it can well retain a stable state.

DISCLOSURE OF THE INVENTION

Accordingly, an object of the present invention is to provide an indomethacin external preparation that has an excellent use feeling and excellent absorbability of indomethacin and that undergoes no phase separation of the preparation with time so that it can well retain a stable state. More particularly, an object of the present invention is to provide an indomethacin external preparation that is compounded with oil component in an amount sufficient for the preparation to provide a satisfactory use feeling in spite of alcohol compounded in the preparation in an amount sufficient for dissolving indomethacin and that causes no phase separation into an oil layer and an aqueous layer so that it has excellent stability with time.

Taking into consideration the above-mentioned points, the inventors of the present invention have made extensive studies. As a result, they have found that compounding an indomethacin preparation containing 25 to 50 wt % of alcohol sufficient for dissolving indomethacin therein and 5 to 30 wt % of oil component sufficient for preventing the occurrence of irregularities therein upon use or sticking thereof after use with 0.01 to 10 wt % of one or more components selected from the group consisting of glyceryl monostearate, sorbitan monostearate, stearyl alcohol, and polyethylene glycol monostearate prevents the phase separation with time of the preparation, thereby accomplishing the present invention.

That is, according to the present invention, the following are provided:

(1) An indomethacin external preparation containing: 0.1 to 3 wt % of indomethacin; 25 to 50 wt % of alcohol; 0.01 to 5 wt % of gelling agent; 5 to 30 wt % of oil component; 20 to 50 wt % of water; and 0.01 to 10 wt % of one or more components selected from the group consisting of glyceryl monostearate, sorbitan monostearate, stearyl alcohol, and polyethylene glycol monostearate.

BEST MODE FOR CARRYING OUT THE INVENTION

Hereinafter, the present invention will be described in detail.

An indomethacin external preparation of the present invention contains: 0.1 to 3 wt % of indomethacin; 25 to 50 wt % of alcohol; 0.01 to 5 wt % of gelling agent; 5 to 30 wt % of oil component; 20 to 50 wt % of water; and 0.01 to 10 wt % of one or more components selected from the group consisting of glyceryl monostearate, sorbitan monostearate, stearyl alcohol, and polyethylene glycol monostearate.

An indomethacin external preparation of the present invention has an excellent use feeling and excellent absorbability and causes no phase separation into an oil layer and an aqueous layer, thus exhibiting satisfactory stability of preparation with time.

The content of indomethacin in the preparation of the present invention is usually 0.1 to 3 wt %, preferably 0.2 to 2 wt %, and particularly preferably 0.5 to 1.5 wt % based on the total weight of the preparation.

In the present invention, the alcohol is preferably lower alcohol, and more preferably alcohol having 1 to 3 carbon atoms. Examples of the alcohol include methanol, ethanol, isopropanol, and n-propanol. Among them, isopropanol is more preferred.

The content of alcohol is usually 25 to 50 wt %, preferably 30 to 50 wt %, and particularly preferably 30 to 40 wt % based on the total weight of the preparation. If the content of alcohol is less than 25 wt %, dissolution of indomethacin is insufficient so that the absorbability of indomethacin becomes disadvantageously poor. On the other hand, the content of the alcohol above 50 wt % is undesirable since the preparation becomes irritant to the skin and causes phase separation with time of the preparation.

As examples of the gelling agent used in the present invention, acrylic polymers such as carboxyvinyl polymer, cellulose polymers such as hydroxypropylmethylcellulose and ethylcellulose, polyvinyl alcohol, and the like may be given.

The content of the gelling agent is usually 0.01 to 5 wt %, preferably 0.5 to 5 wt %, and particularly preferably 0.5 to 2.5 wt % based on the total weight of the preparation.

As examples of oil component in the present invention, hydrocarbons such as squalane and liquid paraffin, esters such as isopropyl myristate, diisopropyl adipate and octyldodecyl myristate, and the like may be given.

The content of oil component is usually 5 to 30 wt %, preferably 7 to 30 wt %, and particularly preferably 7 to 20 wt % based on the total weight of the preparation.

The content of the additional component(s), i.e., the one or more components selected from the group consisting of glyceryl monostearate, sorbitan monostearate, stearyl alcohol, and polyethylene glycol monostearate is usually 0.01 to 10 wt %, preferably 0.05 to 5 wt %, and particularly preferably 0.1 to 5 wt % based on the total weight of the preparation. The content of the additional component(s) described above is less than 0.01 wt % is undesirable since the phase separation with time of the preparation cannot be prevented. On the other hand, the content of the additional component(s) above 10 wt % is also undesirable since the consistency of the preparation increases to make the preparation stiff, providing an unsatisfactory use feeling.

All the additional components usually have melting points of 40° C. or higher and preferably 50° C. or higher. If the melting points are lower than 40° C., the phase separation with time of the preparation can hardly be prevented and such melting points are undesirable.

"Glyceryl monostearate" used in the present invention means a mixture of α-glyceryl monostearate, β-glyceryl monostearate and other glyceryl fatty ester(s), which is generally used as a base material. Examples of commercially available glyceryl monostearate include Nikkol MGS-A, MGS-B, MGS-F20, and MGS-F40 (trade names; manufactured by Nikko Chemicals Co., Ltd.) and Rheodol MS-165, Rheodol MS-60 (trade names; manufactured by Kao Corporation.).

Further, the sorbitan monostearate used in the present invention is a monostearate obtained by esterification of the hydroxyl groups of sorbitol anhydride with stearic acid. This is generally used as a base material. Examples of commercially available sorbitan monostearate include Nikkol SS-10, SS-10M (trade names; manufactured by Nikko Chemicals Co., Ltd.) and Solgen 50 and Sorman S-300 (trade names; manufactured by Takeda Chemical Industries, Ltd.).

Further, as stearyl alcohol used in the present invention, for example, kalcohl (manufactured by Kao Corporation), Nikkol deodorization stearyl alcohol (manufactured by Nikko Chemicals Co., Ltd.), lanette18 (manufactured by Henkel Japan Ltd.), Conol30 S, Conol30 SS, Conol30 F (manufactured by New Japan Chemical Co., Ltd.), NAA-45, NAA-46 (manufactured by NOF Corporation), and the like are on the market.

The polyethylene glycol monostearate used in the present invention is a substance that is obtained by addition polymerization of stearic acid with ethylene oxide or by esterification of polyethylene glycol with stearic acid and is generally used as a base material. For example, polyethylene glycol monostearate (manufactured by Nikko Chemicals Co., Ltd.) is commercially available.

The content of water in the preparation of the present invention is usually 20 to 50 wt %, preferably 30 to 50 wt %, and particularly preferably 40 to 50 wt % based on the total weight of the preparation.

Note that the indomethacin external preparation of the present invention may contain various optional components as desired. For example, it may contain a neutralizing agent, a preservative agent, a stabilizing agent, a wetting agent and so forth.

Here, as the neutralizing agent, organic acids such as citric acid, phosphoric acid, tartaric acid and lactic acid, inorganic acids such as hydrochloric acid, alkali hydroxides such as sodium hydroxide, amines such as triethanolamine, diethanolamine, and diisopropanolamine, and the like can be given.

Further, as the preserving agent, parahydroxybenzoates, benzalkonium chloride, and the like can be given.

Further, as the stabilizing agent, sodium sulfite, sodium bisulfite, dibutylhydroxytoluene, butylhydroxyanisole, edetic acid, and the like can be given.

Further, as the wetting agent, polyhydric alcohols such as glycerin, ethylene glycol, propylene glycol, oleyl alcohol, 1,3-butylene glycol, isopropylene glycol, polyethylene gylcol, and the like can be given.

The indomethacin external preparation of the present invention has a pH of usually 4 to 8 and preferably 5 to 7 from the viewpoints of the stability of indomethacin, prevention of skin irritation and so forth.

The indomethacin external preparation of the present invention can be prepared by a conventional method. For example, it can be produced by heating an oily base material that contains one or more components selected from the group consisting of glyceryl monostearate, sorbitan monostearate, stearyl alcohol, and polyethylene glycol monostearate, an oil component, and the like at a temperature of 40° C. or higher to completely melt them, mixing the obtained melt with an aqueous base material having compounded therein a gelling agent, water and so forth until a homogeneous mixture is obtained, adding alcohol having dissolved therein indomethacin to the homogeneous mixture, and mixing the resultant until it becomes homogeneous.

EXAMPLES

Hereinafter, the present invention will be described concretely by examples. However, it should not be considered that the present invention is limited to these examples.

Example 1

(1) 5 g of octyldodecyl myristate, 5 g of diisopropyl adipate, and 2 g of glyceryl monostearate (MGS-F20, trade name; manufactured by Nikko Chemicals Co., Ltd.; melting point: 54-58° C.) were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 36.0 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Example 2

(1) 5 g of octyldodecyl myristate, 5 g of diisopropyl adipate, and 0.5 g of sorbitan monostearate (NIKKOL SS-10M, trade name; manufactured by Nikko Chemicals Co., Ltd.; melting point: 55-59° C.) were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 37.5 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Example 3

(1) 5 g of octyldodecyl myristate, 5 g of diisopropyl adipate, and 2 g of stearyl alcohol (stearyl alcohol, trade name; manufactured by Nikko Chemicals Co., Ltd.; melting point: 56-58° C.) were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 36.0 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Example 4

(1) 5 g of octyldodecyl myristate, 5 g of diisopropyl adipate, and 2 g of polyethylene glycol monostearate (40 EO.) (NIKKOL MYS-40, trade name; manufactured by Nikko Chemicals Co., Ltd.; melting point: 42-47° C.) were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 36.0 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Example 5

(1) 5 g of octyldodecyl myristate, 5 g of diisopropyl adipate, 0.5 g of sorbitan monostearate, and 3.5 g of glyceryl monostearate were heated and melted at about 70° C. and the whole was mixed until a homogeneous mixture was obtained.

(2) 1.0 g of carboxyvinyl polymer and 0.5 g of hydroxypropylmethylcellulose 2910 were dispersed in 34.5 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.5 g of diisopropanolamine was added to 5.5 g of water and the mixture was stirred for dissolution and the obtained solution was added to the step (4). The mixture was well dispersed while it was cooled to provide a pale yellowish white gel-cream preparation.

Comparative Example 1

(1) 5 g of octyldodecyl myristate and 5 g of diisopropyl adipate were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 38.0 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Comparative Example 2

(1) 5 g of octyldodecyl myristate and 5 g of diisopropyl adipate, were heated and melted at about 70° C. and the whole was mixed until a homogeneous mixture was obtained.

(2) 2 g of carboxyvinyl polymer and 0.5 g of hydroxypropylmethylcellulose 2910 were dispersed in 37.5 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 1 g of diisopropanolamine was added to 5 g of water and the mixture was stirred for dissolution and the obtained solution was added to the step (4). The mixture was well dispersed while it was cooled to provide a pale yellowish gel-cream preparation.

Comparative Example 3

(1) 5 g of octyldodecyl myristate, 5 g of diisopropyl adipate, and 2 g of polyoxyethylene (50) hydrogenated castor oil (HCO-50, trade name; manufactured by Nikko Chemicals Co., Ltd.; melting point: 22-27° C.) were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 36.0 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Comparative Example 4

(1) 5 g of octyldodecyl myristate, 5 g of diisopropyl adipate, and 2 g of polysorbate 60 (NIKKOL TS-10, trade name; manufactured by Nikko Chemicals Co., Ltd.; melting point: 30-34° C.) were heated and melted at about 70° C. and the whole was mixed until a homogeneous mixture was obtained.

(2) 1.5 g of carboxyvinyl polymer and 0.5 g of hydroxypropylmethylcellulose 2910 were dispersed in 36.0 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 0.8 g of diisopropanolamine was added to 5.2 g of water and the mixture was stirred for dissolution and the obtained solution was added to the step (4). The mixture was well dispersed while it was cooled to provide a pale yellowish white gel-cream preparation.

Comparative Example 5

(1) 5 g of octyldodecyl myristate, 5 g of diisopropyl adipate, and 2 g of polysorbate 60 were heated and melted at about 70° C. and the whole was mixed until a homogeneous mixture was obtained.

(2) 2 g of carboxyvinyl polymer and 0.5 g of hydroxypropylmethylcellulose 2910 were dispersed in 35.5 g of hot water at about 70° C. and then the obtained dispersion was added to the step (1), followed by well mixing the dispersion to emulsify it.

(3) 1 g of indomethacin, 3 g of L-menthol and 1 g of polyethylene glycol 400 were added to 36 g of isopropanol and the mixture was stirred for dissolution. Then, the obtained solution was added to the step (2) and the mixture was well mixed to uniformly disperse.

(4) 1 g of an aqueous solution of 1% ETDA-2NA and 2 g of an aqueous solution of 2% sodium bisulfite were added to the step (3) and the mixture was well mixed.

(5) 1 g of diisopropanolamine was added to 5 g of water and the mixture was stirred for dissolution and the obtained solution was added to the step (4). The mixture was well dispersed while it was cooled to provide a pale yellowish white gel-cream preparation.

Test Example 1

To study phase separation stability of the produced preparation, the respective preparations of Examples 1 to 5 and Comparative Examples 1 to 5 were filled in bottles, respectively, which were stored at 5° C. for 1 month. Then, the state of the preparations after the storage was observed and evaluated by scoring those preparations in which no phase separation into an oil layer and an aqueous layer was observed as "o"

and those preparations in which such phase separation was observed as "x". Table 1 shows the results obtained.

TABLE 1

| | Example 1 | Example 2 | Example 3 | Example 4 | Example 5 | Comparative Example 1 | Comparative Example 2 | Comparative Example 3 | Comparative Example 4 | Comparative Example 5 |
|---|---|---|---|---|---|---|---|---|---|---|
| Indomethacin | 1 | 1 | 1 | 1 | 1 | 1 | 1 | 1 | 1 | 1 |
| Octyldodecyl Myristate | 5 | 5 | 5 | 5 | 5 | 5 | 5 | 5 | 5 | 5 |
| Diisopropyl Adipate | 5 | 5 | 5 | 5 | 5 | 5 | 5 | 5 | 5 | 5 |
| Carboxyvinyl Polymer | 1.5 | 1.5 | 1.5 | 1.5 | 1.0 | 1.5 | 2.0 | 1.5 | 1.5 | 2.0 |
| Hydroxypropyl-Methylcellulose 2910 | 0.5 | 0.5 | 0.5 | 0.5 | 0.5 | 0.5 | 0.5 | 0.5 | 0.5 | 0.5 |
| L-menthol | 3 | 3 | 3 | 3 | 3 | 3 | 3 | 3 | 3 | 3 |
| Polyethylene glycol 400 | 1 | 1 | 1 | 1 | 1 | 1 | 1 | 1 | 1 | 1 |
| Isopropanol | 36 | 36 | 36 | 36 | 36 | 36 | 36 | 36 | 36 | 36 |
| ETDA 2Na | 0.01 | 0.01 | 0.01 | 0.01 | 0.01 | 0.01 | 0.01 | 0.01 | 0.01 | 0.01 |
| sodium bisulfite | 0.04 | 0.04 | 0.04 | 0.04 | 0.04 | 0.04 | 0.04 | 0.04 | 0.04 | 0.04 |
| Diisopropanolamine | 0.8 | 0.8 | 0.8 | 0.8 | 0.5 | 0.8 | 1.0 | 0.8 | 0.8 | 1.0 |
| Water | 44.2 | 45.7 | 44.2 | 44.2 | 43.0 | 46.2 | 45.5 | 44.2 | 44.2 | 43.5 |
| Glyceryl monostearate | 2 | — | — | — | 3.5 | — | — | — | — | — |
| Sorbitan monostearate | — | 0.5 | — | — | 0.5 | — | — | — | — | — |
| Stearyl alcohol | — | — | 2 | — | — | — | — | — | — | — |
| Polyethylene glycol monostearate | — | — | — | 2 | — | — | — | — | — | — |
| Polyoxyethylene (50) hydrogenated castor oil | — | — | — | — | — | — | — | 2 | — | — |
| Polysorbate 60 | — | — | — | — | — | — | — | — | 2 | 2 |
| phase Separation stability (stored for 1 month - 5° C.) | o | o | o | o | o | x | x | x | x | x |

From the results shown in Table 1, it can be seen that the preparations of Examples 1 to 5, in which one or more of glyceryl monostearate, sorbitan monostearate, polyethylene glycol monostearate, and stearyl alcohol were blended showed no phase separation and were stable but the preparations of Comparative Examples 1 to 5 without those compounds showed phase separation.

Therefore, it was revealed that an increase in the compounding amount of the gelling agent as in the case of Comparative Example 2, compounding a surfactant having a melting point below 40° C. as in the cases of Comparative Examples 3 and 4, and an increase in the amount of the gelling agent and compounding a surfactant having a melting point below 40° C. in combination as in the case of Comparative Example 5 were not effective in preventing the phase separation of the preparations.

Test Example 2

To evaluate the use feeling of the preparations of the present invention, experiments were conducted by using a commercially available indomethacin-compounded gel formulation and cream formulation as well as the preparations of Examples 1 and 5. Evaluations of the use feeling were made by checking the sticky feeling and occurrence of irregularities when 0.5 g of each preparation was coated on an arm.

A preparation that gave no sticky feeling was assigned "o", while a preparation that gave sticky feeling was assigned "x". On the other hand, a preparation in which no irregularity occurred was assigned "o" and a preparation in which irregularities occurred was assigned "x" Table 2 shows the results of evaluation of sticky feeling and Table 3 shows the results of evaluation of irregularities.

TABLE 2

| Monitor | Example 1 | Example 5 | commercially available gel formulation | commercially available cream formulation |
|---|---|---|---|---|
| A | o | o | x | o |
| B | o | o | x | o |
| C | o | o | o | o |
| D | o | o | x | o |
| E | o | o | x | o |

TABLE 3

| Monitor | Example 1 | Example 5 | commercially available gel formulation | commercially available cream formulation |
|---|---|---|---|---|
| A | o | o | x | o |
| B | o | o | x | o |
| C | o | o | x | o |
| D | o | o | x | o |
| E | o | o | o | o |

From the results shown in Tables 2 and 3, it can be seen that the preparations of Examples 1 and 5 showed neither sticky feeling nor occurrence of irregularities, giving similar use feeling to that of a cream formulation.

Test Example 3

To evaluate the absorbability of the preparations of the present invention, experiments on the absorbability of indomethacin through a skin were conducted by using a commercially available indomethacin-compounded gel formulation and cream formulation as well as the preparations of Examples 1 and 5. Evaluation of the absorbability was made by coating 0.5 g of each preparation on the shaven belly of a rat to an area of 2 cm×2 cm and measuring the concentration of indomethacin in the skin after 4 hours from the application of the preparation. Table 4 shows the results obtained.

TABLE 4

|  | Example 1 | Example 5 | commercially available gel formulation | commercially available cream formulation |
|---|---|---|---|---|
| Concentration of indomethacin in the skin (μg/g) | 1144 | 1561 | 947 | 189 |

From the results shown in Table 4, it can be seen that the absorption of indomethacin through the skin in the case of the preparations of Examples 1 and 5 was higher than that of the commercially available cream formulation and was equal to or higher than that of the commercially available gel formulation.

From the above-mentioned results, it was confirmed that the preparations of the present invention exhibited satisfactory absorbability of indomethacin through the skin and provided an excellent use feeling.

INDUSTRIAL APPLICABILITY

According to the present invention, provided is an indomethacin external preparation that has an excellent use feeling and excellent absorbability and causes no phase separation into an oil layer and an aqueous layer, thus exhibiting satisfactory stability of preparation with time.

What is claimed is:

1. An indomethacin external preparation comprising: 0.1 to 3 wt % of indomethacin; 25 to 50 wt % of alcohol; 0.01 to 5 wt % of gelling agent; 7 to 30 wt % of oil component; 20 to 50 wt % of water; and 0.01 to 10 wt % of one or more components selected from the group consisting of glyceryl monostearate, sorbitan monostearate, stearyl alcohol, and polyethylene glycol monostearate (40EO), wherein the component selected from the group consisting of glyceryl monostearate, sorbitan monostearate, stearyl alcohol, and polyethylene glycol monostearate (40EO) has a melting point of 40° C. or higher.

2. The indomethacin external preparation according to claim 1, wherein the selected component is glyceryl monostearate, sorbitan monostearate, or stearyl alcohol.

* * * * *